(12) United States Patent
Geary et al.

(10) Patent No.: US 8,440,633 B2
(45) Date of Patent: May 14, 2013

(54) ANTHELMINTIC COMBINATION

(75) Inventors: Timothy G. Geary, Quebec (CA); Peter Rolfe, Gunning (AU)

(73) Assignee: AH USA 42 LLC, New York, NY (US)

( * ) Notice: Subject to any disclaimer, the term of this patent is extended or adjusted under 35 U.S.C. 154(b) by 170 days.

(21) Appl. No.: 12/666,143

(22) PCT Filed: Jun. 16, 2008

(86) PCT No.: PCT/IB2008/001638
§ 371 (c)(1),
(2), (4) Date: Apr. 5, 2010

(87) PCT Pub. No.: WO2009/004432
PCT Pub. Date: Jan. 8, 2009

(65) Prior Publication Data
US 2010/0197624 A1    Aug. 5, 2010

Related U.S. Application Data

(60) Provisional application No. 60/947,015, filed on Jun. 29, 2007.

(51) Int. Cl.
*A61K 31/70* (2006.01)
*A61K 31/50* (2006.01)

(52) U.S. Cl.
USPC ............................................. 514/30; 514/250

(58) Field of Classification Search ................... 514/29, 514/30
See application file for complete search history.

(56) References Cited

FOREIGN PATENT DOCUMENTS

WO        01/76370        10/2001
WO      2004/069242       8/2004

OTHER PUBLICATIONS

PCT International Search Report, PCT/IB2008/001638.
Alka et al., "Efficacy of abamectin against ivermectin-resistant strain of *Trichostrongylus* colubriformis in sheep", Veterinary Parsitology, 121:277-283, 2004.
Lee et al., "Marcfortine and Paraherquamide Class of Anthelmintics: Discovery of PNU-141962", Current Topics in Medicinal Chemistry, 2:779-793, 2002.

*Primary Examiner* — Elli Peselev
(74) *Attorney, Agent, or Firm* — Paul M. Misiak

(57) ABSTRACT

A composition comprising 2-desoxoparaherquamide and abamectin for the treatment of a parasitic infestation in mammals.

6 Claims, No Drawings

ANTHELMINTIC COMBINATION

The present invention relates to a method of treating parasitic infestations, particularly helminth infestations, using a combination of 2-desoxoparaherquamide and abamectin, and to novel anthelmintic compositions comprising these agents as active ingredients.

BACKGROUND TO THE INVENTION

The control of parasitic infections in human and animal populations remains an important global endeavor. The causative organisms may be categorized as endoparasitic members of the classes Nematoda, Cestoidea and Trematoda or phylum Protozoa, or as ectoparasitic members of the phylum Arthropoda. The former comprises infections of the stomach, intestinal tracts, lymphatic system, tissues, liver, lungs, heart and brain. Examples include trichinosis, lymphatic filariasis, onchocerciasis, schistosomiasis, leishmaniasis, trypanosomiasis, giardiasis, coccidiosis and malaria.

The latter, ectoparasites, include lice, ticks, mites, biting flies, fleas and mosquitoes. These often serve as vectors and intermediate hosts to endoparasites for transmission to human or animal hosts.

While certain helminthiases can be treated with known drugs, evolutionary development of resistance necessitates a further search for improved efficacy in next generation anthelmintic agents.

The control of endo and ectoparasites, has long been recognized as an important aspect of human and animal health regimens. Traditional treatments were orally or topically administered and indeed such treatments are still in wide use. The more modern thrust of research, however, has been towards compounds which can be administered orally or parenterally to the animals and which will control endo and ectoparasitic populations by killing individual parasites when they ingest the blood of a treated animal.

Although a number of ectoparasiticides and endoparasiticides are in use, these suffer from a variety of problems, including a limited spectrum of activity, the need for repeated treatment and, in many instances, resistance by parasites. The development of novel endo- and ectoparasiticidic treatments is therefore essential to ensure safe and effective control of a wide range of parasites.

Published International Patent Application WO2001/076370 discusses anthelmintic compositions comprising a spirodioxepinoindole, particularly a paraherquamide or marcfortine derivative or analogue, and a macrocyclic lactone, particularly an avermectin or milbemycin derivative or analogue.

Combinations of agents, which are less prone to resistance, or which are active against a wider range of parasites are especially desired.

BRIEF SUMMARY OF THE INVENTION

An object of the present invention is to provide a method for preventing or treating parasitic diseases in mammals which can be broadly used against parasites which are typically resistant to macrocyclic lactones and other classes of anthelmintics. Still another object of the present invention is to provide novel anthelmintic compositions. A further object of the present invention is to provide a method for producing a medicament using a novel composition of the present invention.

In a first embodiment, the present invention provides a method for the treatment of parasitic infestations in mammals, comprising the step of simultaneously or sequentially administering to the mammal effective amounts of (a) 2-desoxoparaherquamide; and (b) abamectin.

In another embodiment, the present invention provides an anthelmintic composition comprising: (a) 2-desoxoparaherquamide; and (b) abamectin. The composition may optionally further comprise a pharmaceutically acceptable carrier.

In another embodiment, the present invention provides the above-described composition for use as a medicament.

In another embodiment, the present invention provides the use of the above-described composition to prepare a medicament for the treatment or prevention of parasitic diseases in mammals.

In another embodiment, the present invention provides a kit comprising: (a) a composition comprising 2-desoxoparaherquamide and optionally a pharmaceutically acceptable carrier; and (b) abamectin and optionally a pharmaceutically acceptable carrier, for sequential administration to a mammal.

In another embodiment, the present invention provides a method for reducing the frequency of macrocyclic lactone-resistant individuals in populations of trichostrongyloid nematodes comprising the step of treating such populations with an effective amount of (a) 2-desoxoparaherquamide; and (b) abamectin.

DETAILED DESCRIPTION OF THE INVENTION

The present invention is directed to the prevention and treatment of parasitic attack on host mammals and provides a new tool for the control of parasitic organisms. In particular, the present invention provides for such a method of treatment comprising the use of:

2-desoxoparaherquamide; and
abamectin.

The mammal may be a human or non-human mammal. Non-human mammals include food animals, farm animals and companion animals, for example, cattle, sheep, goats, pigs, horses, deer, dogs and cats. The method of treatment is particularly applicable to sheep and goats, especially sheep.

The method of treatment can be utilized for treatment of a wide range of parasitic organisms. Further, it should be noted that treatment is achieved in animals with existing parasitic infections by eliminating the existing parasites.

Representative parasitic organisms include the following:

Nemathelminthes, including, for example, *Ancylostoma, Angiostrongylus, Anisakis, Ascaris, Brugia, Bunostomum, Cooperia, Chabertia, Cyathostomum, Cylicocyclus, Dictyocaulus (lungworm), Dipetalonema, Dirofilaria (heartworm), Dracunculus, Elaeophora, Gaigeria, Globocephalus urosubulatus, Haemonchus, Metastrongylus (lungworm), Muellerius (lungworm), Necator americanus, Nematodirus, Oesophagostomum, Onchocerca, Ostertagia, Parascaris, Protostrongylus (lungworm), Setaria, Stephanofilaria, Syngamus, Teladorsagia, Toxascaris, Toxocara, Trichinella, Trichostrongylus, Trichuris, Uncinaria stenocephala,* and *Wuchereria bancrofti;*

Arthropoda, including, for example, Crustacea such as *Argulus* and *Caligus*, Arachnida such as *Amblyomma americanum* (Lone-star tick), *Amblyomma maculatum* (Gulf Coast tick), *Argas persicus* (fowl tick), *Boophilus microplus* (cattle tick), *Demodex bovis* (cattle follicle mite), *Demodex canis* (dog follicle mite), *Dermacentor andersoni* (Rocky Mountain spotted fever tick), *Dermacentor variabilis* (American dog tick), *Dermanyssus gallinae* (chicken mite), *Ixodes ricinus* (common sheep tick), *Knemidokoptes gallinae* (deplumming mite), *Knemidokoptes mutans* (scaly-leg mite), *Otobius megnini* (ear tick), *Psoroptes equi* (scab mite), *Psoroptes ovis* (scab mite), *Rhipicephalus sanguineus* (brown dog tick), and *Sarcoptes scabiei* (mange mite), Insecta such as *Aedes* (mosquito), *Anopheles* (mosquito), *Culex* (mosquito), *Culiseta* (mosquito), *Bovicola bovis* (cattle biting louse), *Callitroga* hominivorax (blowfly), *Chrysops* spp. (deer fly), *Cimex lectularius* (bed bug), *Culicoides* spp. (midges, sandflies, punkies, or no-see-ums), *Damalinia ovis* (sheep biting louse), *Dermaobia* spp. (warble fly), *Gasterophilus haemorrhoidalis* (nose hot fly), *Gasterophilus intestinalis* (common horse hot fly), *Gasterophilus nasalis* (chin fly), *Glossina* spp. (tsetse fly), *Haematobia irritans* (horn fly, buffalo fly), *Haematopinus asini* (horse sucking louse), *Haematopinus eurysternus* (short nosed cattle louse), *Haematopinus ovilius* (body louse), *Haematopinus suis* (hog louse), *Hydrotaea irritans* (head fly), *Hypoderma bovis* (bomb fly), *Hypoderma lineatum* (heel fly), *Linognathus ovillus* (body louse), *Linognathus pedalis* (foot louse), *Linognathus vituli* (long nosed cattle louse), *Lucilia* spp. (maggot fly), *Melophagus ovinus* (sheep ked), *Oestrus ovis* (nose hot fly), *Phormia regina* (blowfly), *Solenopotes capillatus* (little blue cattle louse).

The method of treatment is particularly useful for the control of helmith parasites, including Nemathelminthes.

2-Desoxoparaherquamide (alternatively known as 2-deoxyparaherquamide) is disclosed in U.S. Pat. No. 5,750,695, and its synthesis is described in Example 37 of that patent. The structural formula of 2-desoxoparaherquamide is shown in formula (I).

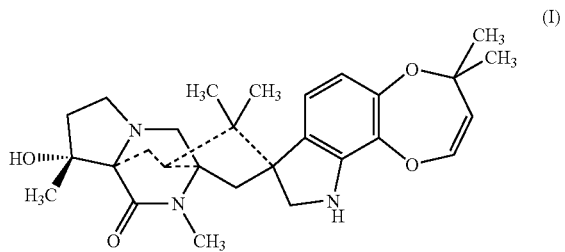

(I)

Abamectin (alternatively known as avermectin $B_1$) is disclosed in U.S. Pat. No. 4,310,519. It is a mixture of avermectin $B_{1a}$ (formula (IIa)) and avermectin $B_{1b}$ (formula (IIb)), wherein at least 80% of the mixture is the $B_{1a}$ component.

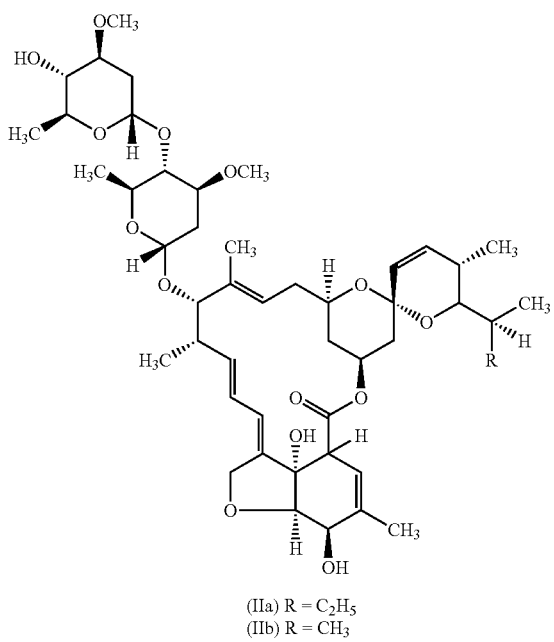

(IIa) R = $C_2H_5$
(IIb) R = $CH_3$

The two components may be administered simultaneously or sequentially. As used herein, simultaneous administration means the administration of both components to the host animal in a single action, which requires the two components to be incorporated into a single dosage form, such as a single oral solution or suspension, tablet or pour-on solution.

Sequential administration means the administration of each component is a separate action, but the two actions are linked. For example, administering a tablet comprising one component and a second tablet comprising the second component is considered to be sequential administration, even if the two tablets are given to the host animal at the same time. For example, administering a liquid formulation comprising one component and a second liquid formulation comprising the second component is considered to be sequential administration, if the formulations are given to the host animal at the same time or if one formulation is given to the host animal immediately or shortly after the administration of the other formulation.

For convenience, simultaneous administration may be preferable.

The exact dosage and frequency of administration of the two agents depend on many factors, including (but not limited to) the severity of the particular condition being treated, the age, weight, and general physical condition of the particular patient (human or animal), and other medication the patient may be taking. These factors are well known to those skilled in the art, and the exact dosage and frequency of administration can be more accurately determined by measuring the concentration of the inventive composition in the patient's blood and/or the patient's response to the particular condition being treated.

In general, the amount of the 2-desoxoparaherquamide (2-DOPH) to be administered ranges from about 0.05 to 20 mg per kg of animal body weight, such total dose being given at one time or in divided doses over a relatively short period of time such as 1-5 days. Excellent control of parasites is obtained in animals by administering from about 0.1 to 10.0 mg per kg of body weight in a single dose. More specifically, the dose is about 0.25 to 2 mg per kg of body weight in a single dose. Most specifically, the dose is about 2 mg per kg of body weight in a single dose.

The amount of abamectin to be administered ranges from about 0.001 to 10 mg per kg of animal body weight, such total dose being given at one time or in divided doses over a relatively short period of time such as 1-5 days. Excellent control of such parasites is obtained in animals by administering from about 0.025 to 0.5 mg per kg of body weight in a single dose. More specifically, the dose is about 0.025 to 0.2 mg per kg of body weight in a single dose; most specifically, the dose is about 0.2 mg per kg of body weight in a single dose. Repeat treatments may be given as required to combat re-infections and are dependent upon the species of parasite and the husbandry techniques being employed. The techniques for administering these materials to animals are known to those skilled in the veterinary field.

The agents may be administered by any suitable route, including oral, parenteral or topical administration. When the two agents are administered sequentially then they may be administered by different routes. The agents will generally be incorporated into formulations further comprising suitable excipients, wherein the formulations are adapted to the route of administration intended. When the two agents are administered simultaneously then they are incorporated into a single formulation.

For oral administration the agents may be administered in a dosage form such as a solution, suspension, capsule, bolus, tablet or medicated feed additive as examples. The solid dosage forms (i.e., non-liquid) comprise the active ingredients mixed with functional excipients. These excipients are well known to those skilled in the art of producing capsules, tablets, boluses or solid medicated feed additives. These solid dosage forms are prepared by different methods depending on the dosage form being produced. Those skilled in manufacturing of the formulations will be familiar with the procedures.

Capsules are generally prepared by blending the active with a filler/bulking powder (e.g., lactose, microcrystalline cellulose) and potentially other excipients such as glidants/lubricants to aid in the flow of the powder (e.g., magnesium stearate, steric acid) and/or disintegration (e.g., sodium starch glycolate, starch) of the capsule. This flowable powder containing the active is then filled in to hard-shell capsules. Another type of capsule are referred to as soft gelatin capsules (i.e., soft-gels). These are prepared by mixing the active with a liquid carrier such as an oil (e.g., corn oil, sesame oil, fractionated coconut oil) and then filled in to the soft capsule.

Tablets are a second type of solid dosage form which could be used. Tablets use excipients that are diluents/fillers (lactose, dicalcium phosphate, microcrystalline cellulose), disintegrating agents (starch, sodium carboxymethylcellulose), binders (polyvinyl pyrrolidone, methyl cellulose) and lubricants/glidants (steric acid, magnesium stearate). Three main methods of producing tablets are utilized including direct compression, dry granulation and wet granulation. In direct compression all the excipients and active are blended together to produce a homogeneous mixture. This blended powder is then fed in to a tableting machine that produces tablets via compression of defined amount of powder in to an individual unit tablet. Dry granulation includes mixing the excipients with the active and then putting this homogenous mixture through a roller compactor. The roller compactor will produce large compacts or ribbons that can then be reduced in size with a mill. It is these smaller granules that will then flow well and can be placed in to a tableting machine to produce tablets. The wet granulation method includes mixing the active agent and excipients and then adding a liquid (water, alcohol) via spraying or mixing. This liquid often also includes the binder agent. This mixture of solid and liquid is forced through a screen to produce granules and dried if using a traditional granulating process. Or, if using a fluid bed dryer the granulation is dried in the fluid bed dryer. These granules if needed are further reduced in size with a mill and then blended with a lubricant and fed in to a tableting machine to produce tablets.

Boluses are another potential dosage form. Boluses in this patent mean either large tablets intended for administration to large animals produced by the processes mentioned above or some similar fashion. Or, large solid dosage forms that are given orally to animals that may be different from conventional tablets.

Solid feed additives are another potential dosage forms. These products are produced by mixing the active agents with suitable feed carriers (rice hulls, soybean hulls, dicalcium phosphate) to produce a Medicated Type A Article sometimes called a premix. Often times mineral oil is also included to minimize dusting. These Medicated Type A Articles or feed additives are further diluted by placing them in to the feeds which are consumed by the animals. Another version of these feed additives are formed in to feed blocks containing the drug which can then be licked by the animals to consume the active agent.

More preferably, liquid formulations for oral administration are contemplated. Accordingly, the agents may be formulated as a suspension, solution or emulsion in a suitable aqueous or non-aqueous liquid vehicle. Non-aqueous vehicles could include, but not limited to, polyethylene glycol, glycerol formal, triacetin, propylene glycol, n-methyl pyrrolidone and various oils (e.g., peanut, mineral, olive, fractionated coconut, sunflower, soybean, corn). Sometimes the oils of choice are called medium chain triglycerides with tradenames such as Miglyol®810/820 or Captex®355. Another liquid of choice is esters of propylene glycol like propylene glycol di-capryloate (Miglycol®840). These non-aqueous vehicles may contain microbial preservatives (e.g., alcohol) and chemical stabilizers (e.g., butylhydroxytoluene, vitamin E). Aqueous vehicles would be water with certain agents such as flavor enhancers (fruit flavors, sucrose, glucose), microbial preservatives (benzyl alcohol, benzoic acid, benzalkonium chloride, buffers (citrate, phosphate) or pH adjustors (hydrochloric acid, sodium hydroxide). These liquid dosage forms are prepared by dispersing or dissolving the active agents in to the carrier liquid vehicles by mixing to create either a suspension or solution. Liquids that are miscible could also be combined to produce co-solvents and act as the carrier vehicle. In some cases nonmiscible liquids could be combined with an appropriate emulsifying agent (e.g., lecithin), if needed to create a microemulsion or emulsion.

Examples of parenteral administration include intramuscular, intraperitoneal, intravenous or subcutaneous injection in which the active ingredients are dissolved or dispersed in a liquid carrier vehicle or implant and injected in to the body. For parenteral administration using a liquid, the active materials are suitably mixed with an acceptable vehicle which is either aqueous or nonaqueous. For parenteral administration with an implant the active is formulated in to either a solid or liquid implant which is parenterally administered. Parenteral aqueous dosage forms would be composed of water along with, if needed, buffers (e.g., citrate, phosphate), pH adjustors (hydrochloric acid, sodium hydroxide), microbial preservatives (e.g., benzyl alcohol, benzoic acid, benzalkonium chloride and chemical stability preservatives (e.g., antioxidants such as propyl gallate, ascorbic acid). Parenteral nonaqueous dosage forms could use, but not limited to, polyethylene glycol, glycerol formal, triacetin, n-methyl pyrrolidone, 2-pyrrolidone and various oils (e.g., peanut, mineral, olive, fractionated coconut, sunflower, soybean, corn). These nonaqueous parenteral dosage forms could also include microbial preservatives, and chemical stabilizing agents. Cosolvents (i.e., two or more solvents) may also be used. In addition, combining of immiscible solvents to create emulsions may be another dosage form for parenteral administration. Parenteral dosage forms are produced by mixing the active agent with the respective liquid and any other excipients. This mixing is either done under aseptic conditions with a final filtering through 0.22 micron filters to produce a sterile product or subjecting the final product to terminal sterilization (e.g., heat, gamma irradiation) to create a sterile product for injection.

For topical administration the agents may, for example be formulated as a pour-on or spot-on dosage form. The same aqueous and nonaqueous vehicles mentioned above could be utilized. Viscosity enhancing additives (e.g., carboxymethylcellulose, waxes) could also be utilized to add in retention on the animal or penetration enhancers (e.g., alcohols) to aid in gaining systemic absorption could be included. The topical dosage forms are produced using methods well know to those skilled in the art. In a simple method, the active agent is mixed with the solvents along with any additives to create a solution or suspension which can then be poured or spotted on to the animal.

Parasiticide dosage forms for animals are sometimes are called drench products. The "drench" dosage form could either be given topically or orally. The "drench" term is used because the liquid dosage form is administered all-at-once either into the mouth/throat of the animal or poured (e.g., drenched) on to the skin/fur of the animal. This patent is meant to include drench formulations.

Such dosage formulations as mentioned above (e.g., suspensions, solutions, capsules, tablets, emulsion, boluses and solid feed additives) may be varied widely with respect to their total weight and content of the antiparasitic agent depending upon factors such as the type of host animal to be treated, the severity and type of infection and the weight of the host.

The agents may be used in combination with one or more additional active agents, and these agents may be incorporated as part of the formulation for administration. Suitable further active agents include benzimidazoles (such as albendazole, cambendazole, fenbendazole, flubendazole, mebendazole, oxfendazole, oxibendazole and parbendazole), imidazothiazoles (such as tetramisole, levamisole), and tetrahydropyrimidines (such as pyrantel pamoate, oxantel or morantel), nitroscanate, antiparasitic oxazolines (such as those disclosed in U.S. Pat. No. 5,478,855, U.S. Pat. No. 4,639,771 and DE-19520936), derivatives and analogues of the general class of dioxomorpholine antiparasitic agents as described in WO-9615121, cyclic depsipeptides (such as those described in WO-9611945, WO-9319053, WO-9325543, EP-626375, EP-382173, WO-9419334, EP-382173, and EP-503538, and particularly emodepside), fipronil; pyrethroids; organophosphates; insect growth regulators (such as lufenuron); ecdysone agonists (such as tebufenozide and the like); spinosyns (such as Spinosad), amidoacetonitriles (such as those disclosed in WO-2005044784); neonicotinoids (such as imidacloprid and the like); organophosphates (such as trichlorphon, napthalophos, pyraclophos); salicylanilides (such as closantel, niclosamide); Benzoenedisulphonmaide (such as clorsulon); and pyrazinaisoquinoline (such as praziquantel).

For sequential administration, the compositions comprising the active agents may conveniently be presented in kit form. Such a kit comprises two or more separate pharmaceutical compositions, at least one of which contains 2-desoxoparaherquamide and one contains abamectin, and means for separately retaining said compositions, such as a container, divided bottle, or divided foil packet.

The kit of the invention is particularly suitable for administering different dosage forms, for example, oral and parenteral, for administering the separate compositions at different dosage intervals, or for titrating the separate compositions against one another.

While not wishing to be bound to any specific scientific theory, it is believed that the combination of 2-desoxoparaherquamide with abamectin is able to specifically reduce the frequency of alleles encoding resistant proteins in trichostrongyloid populations, thus maintaining and restoring to utility the proteins for trichostrongyloid control.

EXAMPLE 1

The efficacy of the combination is demonstrated in the following trial.

Fifty four (54) sheep (Merino whether hoggets) were assigned at random to one of nine groups. At day -41 of the trial the sheep were treated with naphthalaphos and levamisole to remove any pre-existing parasite burden. Faecal samples were collected at day -27 of the trial and analysed to confirm parasite eradication. On day -24 the sheep were infected by intra-ruminal injection with the following parasites:

ca. 3000 $3^{rd}$ stage (L3) Kirby susceptible strain *Haemonchus contortus*
ca. 6000 $3^{rd}$ stage (L3) McMaster susceptible strain *Teladorsagia circumcincta*
ca. 6000 $3^{rd}$ stage (L3) McMaster susceptible strain *Trichostrongylus colubriformis*

Faecal samples were collected on day -1 of the trial and egg counts were determined.

On day 0 of the trial, the sheep were treated according to the following schedule.

| Group | Number of animals | Formulation | Dose of 2-DOPH* | Dose of ABA* |
|---|---|---|---|---|
| G1 | 6 | No treatment (negative control) | 0 | 0 |
| G2 | 6 | F1 | 2 mg/kg | 0.2 mg/kg |
| G3 | 6 | F1 | 1 mg/kg | 0.1 mg/kg |
| G4 | 6 | F1 | 0.5 mg/kg | 0.05 mg/kg |
| G5 | 6 | F1 | 0.25 mg/kg | 0.025 mg/kg |
| G6 | 6 | F2 | 2 mg/kg | 0.2 mg/kg |
| G7 | 6 | F2 | 1 mg/kg | 0.1 mg/kg |
| G8 | 6 | F2 | 0.5 mg/kg | 0.05 mg/kg |
| G9 | 6 | F2 | 0.25 mg/kg | 0.025 mg/kg |

*2-DOPH = 2-desoxoparaherquamide; ABA = abamectin

Formulation F1 comprises 2-DOPH (10 mg/mL), ABA (1.0 mg/mL), glycerol formal (50 mg/mL), butylhydroxytoluene (0.5 mg/mL), and triacetin (1096.8 mg/mL).

Formulation F2 comprises 2-DOPH (10 mg/mL), ABA (1.0 mg/mL), glycerol formal (50 mg/mL), butylhydroxytoluene (0.5 mg/mL), triacetin (400 mg/mL) and propylene glycol di-capryloate (550.8 mg/mL).

Two animals from each group were sacrificed on each of days 13, 14 and 15 of the trial. Gastrointestinal organs and faecal samples were analysed for evidence of remaining parasitic infestation.

| | Faecal egg count | |
|---|---|---|
| Group | Group geometric mean egg count | % Efficacy |
| G1 | 11921.4 | |
| G2 | 0.9 | 99.99 |
| G3 | 0.0 | >99.99 |
| G4 | 1.1 | 99.99 |
| G5 | 37.6 | 99.68 |
| G6 | 0.0 | >99.99 |
| G7 | 0.9 | 99.99 |
| G8 | 0.0 | >99.99 |
| G9 | 11.3 | 99.90 |

| | Total worm count | | | | | |
|---|---|---|---|---|---|---|
| | *Haemonchus contortus* | | *Teladorsagia circumcincta* | | *Trichostrongylus colubriformis* | |
| Group | Geometric mean worm count | % Efficacy | Geometric mean worm count | % Efficacy | Geometric mean worm count | % Efficacy |
| G1 | 801.7 | | 2208.4 | | 2539.0 | |
| G2 | 0.0 | >99.99 | 0.0 | >99.99 | 0.0 | >99.99 |
| G3 | 0.0 | >99.99 | 0.0 | >99.99 | 0.0 | >99.99 |
| G4 | 0.0 | >99.99 | 0.0 | >99.99 | 0.7 | 99.97 |
| G5 | 2.1 | 99.74 | 110.1 | 95.02 | 26.8 | 98.94 |
| G6 | 0.7 | 99.92 | 0.7 | 99.97 | 0.0 | >99.99 |
| G7 | 0.0 | >99.99 | 0.0 | >99.99 | 0.0 | >99.99 |
| G8 | 0.7 | 99.92 | 0.0 | >99.99 | 0.0 | >99.99 |
| G9 | 1.1 | 99.87 | 50.6 | 97.71 | 6.1 | 99.76 |

EXAMPLE 2

The Treatment of Resistant Strains of Gastrointestinal Parasites in Sheep

Sheep were artificially infected with L3 larvae of *Teladorsagia* (Ostertagia) *circumcincta* and *Trichostrongylus colubriformis* and efficacy was measured by total worm counts in the treatment group compared to the control group following administration of treatment. The animals were treated as outlined below with the commercially available reference products included to confirm the resistance profile of the above parasites.

| Trt. Grp. | Test/Reference Item | Dose Rate | Dose Volume | Route | Freq. | Trt. Day | No. of Animals |
|---|---|---|---|---|---|---|---|
| T01 | Placebo (tap water) | N/A | 0.20 mL/kg | Per os | Once | Day 0 | 10 |
| T02 | 2-DOPH plus Abamectin | 2 mg/kg 0.2 mg/kg | 0.20 mL/kg | Per os | Once | Day 0 | 10 |
| T03 | Albendazole | 3.8 mg/kg | 0.15 mL/kg | Per os | Once | Day 0 | 10 |
| T04 | Levamisole | 8 mg/kg | 0.20 mL/kg | Per os | Once | Day 0 | 10 |
| T05 | Ivermectin | 0.2 mg/kg | 0.25 mL/kg | Per os | Once | Day 0 | 10 |

All study animals were necropsied on Day 15 after treatment. Abomasa and small intestines were collected for worm recovery and total worm count estimations. Group arithmetic mean total worm counts, p-values and treatment efficacies of 2-DOPH/abamectin, albendazole, levamisole and ivermectin against resistant strains of three gastrointestinal nematodes in sheep (15 days post-treatment).

The present study shows zero % efficacy of ivermectin (which is in the same class of compounds as abamectin) against Teladorsagia circumcincta; and 100% efficacy of the combination of 2-DOPH/abamectin against Teladorsagia circumcincta; therefore, this finding is unexpected and unpredicted.

EXAMPLE 3

The Treatment of Resistant Strains of Gastrointestinal Parasites in Sheep

Sheep were artificially infected with infective L3 larvae in a mixed culture containing *Haemonchus contortus, Teladorsagia* spp and *Trichostrongylus* spp, and efficacy was measured by total worm counts in the treatment group compared to the control group following administration of treatment. The animals were treated as outlined below with the commercially available reference products included to confirm the resistance profile of the above parasites.

| | | Total Worm Count | | |
|---|---|---|---|---|
| Treatment Group | Variable | *Teladorsagia circumcincta* | *Teladorsagia trifurcata* | *Trichostrongylus colubriformis* |
| Negative control (T01) | Prevalence | 10/10 | 9/10 | 10/10 |
| | Range | 120-3024 | 0-522 | 3040-5740 |
| | Arithmetic Mean | 1689.5 | 230.5 | 4160.0 |
| 2-DOPH/abamectin (T02) | Prevalence | 0/10 | 0/10 | 0/10 |
| | Range | 0-0 | 0-0 | 0-0 |
| | Arithmetic Mean | 0.0 | 0.0 | 0.0 |
| | p-value (vs T01) | <0.0001 | 0.0001 | <0.0001 |
| | % efficacy (arithmetic mean) | 100.00 | 100.00 | 100.00 |
| Albendazole (T03) | Prevalence | 10/10 | 7/10 | 10/10 |
| | Range | 80-3708 | 0-712 | 1320-2660 |
| | Arithmetic Mean | 2184.4 | 281.6 | 1812.0 |
| | p-value (vs T01) | 0.1488 | 0.4526 | <0.0001 |
| | % efficacy (arithmetic mean) | NEG^ | NEG^ | 56.44 |
| Levamisole (T04) | Prevalence | 7/9 | 4/9 | 9/9 |
| | Range | 0-1020 | 0-180 | 300-1500 |
| | Arithmetic Mean | 292.8 | 36.7 | 652.6 |
| | p-value (vs T01) | 0.0003 | 0.0083 | <0.0001 |
| | % efficacy (arithmetic mean) | 82.67 | 84.08 | 84.31 |
| Ivermectin (T05) | Prevalence | 10/10 | 7/10 | 10/10 |
| | Range | 680-3600 | 0-459 | 400-4060 |
| | Arithmetic Mean | 2093.2 | 194.8 | 1860.0 |
| | p-value (vs T01) | 0.2366 | 0.5990 | <0.0001 |
| | % efficacy (arithmetic mean) | NEG^ | 15.49 | 55.29 |

^NEG = negative efficacy; efficacy not calculated as the mean count was higher in the treated group than in the control group (T01)

| Trt. Grp. | Test/Reference Item | Dose Rate | Dose Volume | Route | Freq. | Trt. Day | No. Animals |
|---|---|---|---|---|---|---|---|
| T01 | Placebo (tap water) | N/A | 0.2 mL/kg | Per os | Once | Day 0 | 10 |
| T02 | 2-DOPH plus Abamectin | 2 mg/kg 0.2 mg/kg | 0.2 mL/kg | Per os | Once | Day 0 | 10 |
| T03 | Albendazole | 3.8 mg/kg | 0.15 mL/kg | Per os | Once | Day 0 | 10 |
| T04 | Levamisole | 8 mg/kg | 0.20 mL/kg | Per os | Once | Day 0 | 10 |
| T05 | Ivermectin | 0.2 mg/kg | 0.25 mL/kg | Per os | Once | Day 0 | 10 |

All study animals were necropsied on Day 15 after treatment. Abomasa and small intestines were collected for worm recovery and total worm count estimations.

| | Total Worm Count | | |
|---|---|---|---|
| Treatment Group | Variable | *Haemonchus contortus* | *Teladorsagia* spp (total)§ | *Trich. colubriformis* |
|---|---|---|---|---|
| Negative control (T01) | Prevalence | 9/10 | 10/10 | 10/10 |
| | Range | 0-1660 | 20-3860 | 4250-6228 |
| | Arithmetic Mean | 844.0 | 1410.0 | 5103.8 |
| 2-DOPH/abamectin (T02) | Prevalence | 0/10 | 5/10 | 1/10 |
| | Range | 0-0 | 0-400 | 0-20 |
| | Arithmetic Mean | 0.0 | 78.0 | 2.0 |
| | p-value (vs T01) | <0.0001 | 0.0005 | <0.0001 |
| | % efficacy (arithmetic mean) | 100 | 94.47 | 99.96 |
| Albendazole (T03) | Prevalence | 8/10 | 10/10 | 10/10 |
| | Range | 0-320 | 160-1200 | 2600-5160 |
| | Arithmetic Mean | 164.0 | 590.0 | 3828.0 |
| | p-value (vs T01) | <0.0001 | 0.0350 | <0.0001 |
| | % efficacy (arithmetic mean) | 80.57 | 58.16 | 25.00 |
| Levamisole (T04) | Prevalence | 1/10 | 8/10 | 10/10 |
| | Range | 0-20 | 0-160 | 2120-5800 |
| | Arithmetic Mean | 2.0 | 52.0 | 4320.7 |
| | p-value (vs T01) | <0.0001 | 0.0004 | 0.0817 |
| | % efficacy (arithmetic mean) | 99.76 | 96.31 | 15.34 |
| Ivermectin (T05) | Prevalence | 8/10 | 10/10 | 10/10 |
| | Range | 0-940 | 280-3800 | 3140-5920 |
| | Arithmetic Mean | 442.0 | 1680.0 | 4510.0 |
| | p-value (vs T01) | 0.0020 | 0.6068 | 0.0761 |
| | % efficacy (arithmetic mean) | 47.63 | NEG | 11.63 |

The above example shows an additional study demonstrating the high efficacy of the 2-DOPH/abamectin combination in the face of resistance to the macrocyclic lactone class of compounds.

The invention claimed is:

1. An oral anthelmintic composition comprising effective amounts of 2-desoxoparaherquamide and abamectin wherein said composition provides a dose ranging from about 0.5 to 2 mg/kg of 2-desoxoparaherquamide and from about 0.05 to 0.2 mg/kg of abamectin.

2. The composition of claim 1 further comprising a pharmaceutically acceptable carrier.

3. A method for treating an endoparasitic infestation in a mammal comprising the step of orally administering to the mammal an effective amount of a composition comprising 2-desoxoparaherquamide at about 0.5 to 2 mg/kg and abamectin at about 0.05 to 0.2 mg/kg.

4. The method of claim 3, wherein the parasite is a helminth.

5. The method of claim 4, wherein the helminth is a trichostrongyloid nematode.

6. The method of claim 3 wherein the mammal is a sheep.

* * * * *